United States Patent [19]

Mesek et al.

[11] 4,352,355

[45] Oct. 5, 1982

[54] DIAPER WITH CONTOURED PANEL AND CONTOURED ELASTIC MEANS

[75] Inventors: Frederick K. Mesek; Virginia R. Mesek, both of Oak Forest, Ill.

[73] Assignee: Johnson & Johnson Baby Products Company, New Brunswick, N.J.

[21] Appl. No.: 146,838

[22] Filed: May 5, 1980

Related U.S. Application Data

[63] Continuation-in-part of Ser. No. 892,628, Apr. 3, 1978, abandoned.

[51] Int. Cl.³ ............................................. A61F 13/16
[52] U.S. Cl. .................................... 128/287; 128/284
[58] Field of Search ................. 128/284, 287, 290 P

[56] References Cited

U.S. PATENT DOCUMENTS

| | | | |
|---|---|---|---|
| 2,577,398 | 12/1951 | Blake | 128/287 |
| 2,754,824 | 7/1956 | Blaufus | 128/284 |
| 3,039,466 | 6/1962 | Wilson | 128/287 |
| 3,417,751 | 12/1968 | Murdoch | 128/287 |
| 3,828,367 | 8/1974 | Bourgeors | 2/224 A |
| 3,860,003 | 1/1975 | Buell | 128/287 |
| 4,050,462 | 9/1977 | Woon et al. | 128/287 |
| 4,081,301 | 3/1978 | Buell | 128/287 |

FOREIGN PATENT DOCUMENTS

| | | | |
|---|---|---|---|
| 1388974 | 1/1965 | France | 128/287 |
| 2063794 | 7/1971 | France | 128/287 |
| 2335165 | 7/1977 | France | 128/287 |
| 282061 | 7/1962 | Switzerland | 128/287 |

*Primary Examiner*—Lee S. Cohen
*Assistant Examiner*—C. W. Shedd
*Attorney, Agent, or Firm*—Martha A. Michaels

[57] ABSTRACT

A disposable diaper having an absorbent batt with an intermediate portion of reduced width and elastic means adjacent to each side of the batt and generally parallel therewith. The intermediate portion of the batt preferably is offset toward one end of the diaper, and may include relatively short rectilinear batt side segments. Further batt side segments extend outwardly at an angle from the ends of the rectilinear batt side segments, and still further rectilinear batt end segments extend outwardly from the ends of the inclined batt side segments.

4 Claims, 6 Drawing Figures

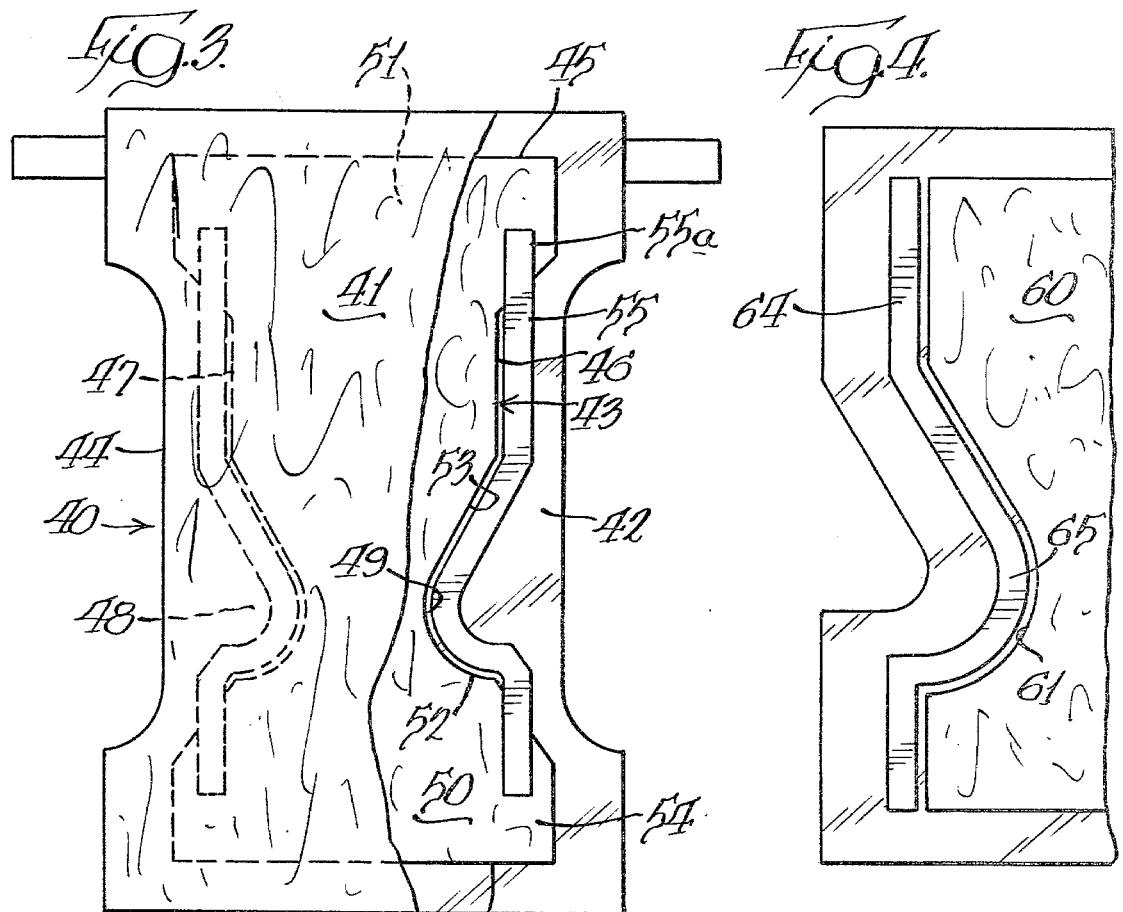

DIAPER WITH CONTOURED PANEL AND CONTOURED ELASTIC MEANS

The present invention is a continuation-in-part application of copending patent application U.S. Ser. No. 892,628 filed Apr. 3, 1978, now abandoned.

BACKGROUND OF THE INVENTION

The present invention relates to improvements in disposable diapers which enable the diaper to closely conform to the torso of a baby without causing any discomfort to the baby, while at the same time providing improved gasketing around the thighs and resultant fluid containment.

In the recent past disposable diapers have been introduced into the marketplace which have a narrow but relatively thick strip of elastic at each side thereof, so as to gather the side margins of the facing and backing layers of the diaper without gathering the absorbent panel thereof. Such diapers have an hourglass shaped absorbent panel, and are made generally in accordance with the teachings of U.S. Pat. No. 3,860,003. In order for the elastic members to be effective in such diapers, it is necessary that the elastic members be parallel with one another and spaced relatively far from the side marginal edges of the absorbent panel of the diaper, and for the elastic members to be associated with thin, highly flexible facing and backing layers. As a result, when such diapers are placed upon a baby, the narrow but relatively thick elastic members cause a narrow band of the facing layer to bear against the baby's skin with substantial line contact. This results in a high degree of stress concentration that may cause pinching and irritation of the baby's skin.

The problems attributable to the unduly high compressive force caused by such narrow but relatively thick elastic strips of the prior art diapers mentioned above are particularly acute when the baby has voided and the diaper is wet. Because the backing and facing layers are so highly flexible, when the diaper is wet and conditions are present tending to cause hydration of the baby's skin, the narrow elastic members sometimes cause the facing layer to press against the skin with sufficient force to injure the skin. Also, the elastic members in prior art diapers of the type described above cause the diaper to gradually creep upwardly upon the baby's thighs. As a result, the forces applied to the skin by the stressed elastic members increase the longer the diaper is worn.

Thus, the improved fit attributable to diapers having a contoured panel and elasticized side flaps is accomplished only with a sacrifice in comfort to the baby. This result is aggravated by having the elastic members parallel with one another, since such elastic members do not conform to the perineal area of the baby, and when the diaper is applied, higher pressures are applied to the inner sides of the baby's thighs.

While many attempts have been made in the past to provide diapers, both disposable and non-disposable, with improved fit characteristics without sacrificing comfort, heretofore such efforts have not met with success.

SUMMARY OF THE INVENTION

In addition to those elements which are present in currently commercially available products, i.e., a moisture pervious facing adapted to engage the baby's skin, an absorbent batt or panel adjacent to the facing, and an outer moisture impervious backing over the absorbent batt, in the diaper of the present invention the absorbent batt has an intermediate portion of reduced width. Secured constringent means are provided at each side of the diaper which are effective to not only gather the longitudinal margins of the diaper but also which are immediately adjacent the side edges of the batt to reduce the length of the side margins of the absorbent batt and create pillow-like marginal bulges therein by applying constringing forces to the sides of the absorbent batt at least in the intermediate portion. In a preferred embodiment, the constringent means is provided by continuous relatively wide, but thin, elastic members that are secured to the backing and/or facing and are located generally parallel and closely to the side margins of the absorbent batt so that constringing forces generated by the elastic members are transmitted to the sides of the absorbent batt at least in the intermediate portion through the backing and generally throughout the entire length dimension of the absorbent batt, thereby causing the sides of the absorbent batt to buckle and/or bulge. By the term "relatively wide," the present invention contemplates that elastic members have a width of at least $\frac{1}{4}$", preferably a width of at least $\frac{1}{2}$", and more preferably a width from about $\frac{3}{4}$" to about $1\frac{1}{4}$". The width-to-thickness ratio of the constringent means is preferably at least about 100, although lesser width-to-thickness ratios of about 30 may be tolerated for elastic members having a width at the low end of the desired range, provided such elastic members are positioned directly adjacent to the side of the batt.

It is contemplated that the relatively wide elastic members may be provided by two or more relatively narrow ($\frac{1}{4}$" or less) elastic members that are positioned in spaced parallel relationship with respect to one another, and which cooperate to function as though they are essentially one elastic member having a width dimension that is measured between the outer edges of the outer elastic members. And, it is also contemplated that the relatively wide elastic members may be provided by round, or flattened elastic tubes, woven bands, reticulated bands, or elastic monofilaments that are arranged to provide the desired force distribution.

Diapers constructed in accordance with the present invention have several unexpected advantages, particularly as compared to the diapers of the type disclosed in U.S. Pat. No. 3,860,003. In this regard, by utilizing relatively wide elastic members as the constringent means, the area of the facing that is pressed against the baby's skin is relatively large so as to distribute the force applied to the skin over a relatively large area and to minimize the possibility of irritation. Because of the relatively large area of facing engaging the baby's skin and the bulged side margins of the batt, improved gasketing around the thighs is effected, thereby minimizing leakage from the diaper. In this regard, it is significant that absorptive materials effect at least in part the gasketing action, in contradistinction to the relatively non-absorbent facing in U.S. Pat. No. 3,860,003 which provides little, if any gasketing action.

As will appear in more detail from the following description, diapers of the present invention provide improved fit, and improved gasketing (or sealing) around the baby's legs without irritation to the baby's skin.

BRIEF DESCRIPTION OF THE DRAWINGS

In the drawings,

FIG. 3 is a plan view of another embodiment of a disposable diaper of this invention with a portion broken away to show interior detail; and FIGS. 4, 5 and 6 are fragmentary plan views of further embodiments of disposable diapers in accordance with the present invention.

DESCRIPTION OF THE PREFERRED EMBODIMENTS

Figure 1:
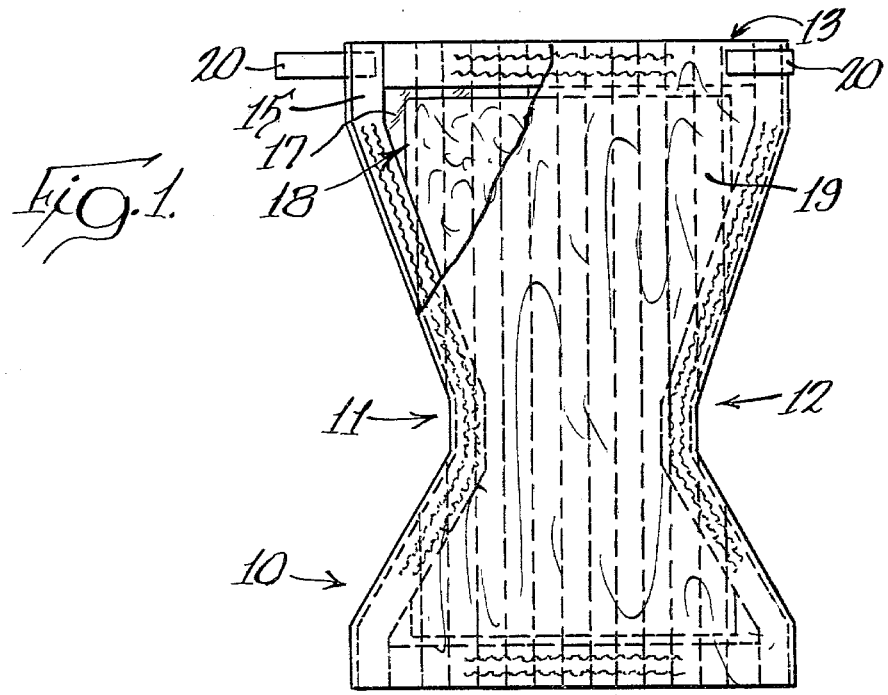
FIG. 1 is a plan view illustrating a disposable diaper as manufactured embodying the present invention, with a portion broken away to show interior detail.

For a disposable diaper of the present invention the constringent means is a readily stretchable, elastic, preferably thermoplastic member of substantial width that possesses a certain minimum elastic recovery.

The term "elastic," as used herein, refers to sheets, films, ribbons and the like which have a recovery of at least 90%, when elongated to within 10% of their yield point and measured in accordance with the following formula:

Percent retration = $(L_e - L_t/L_e - L_o) \times 100$ where
- $L_o$ = original length of sample
- $L_e$ = fully extended length
- $L_t$ = length of sample measured 3 seconds after released from extended length.

The thickness of the elastic member generally is 10 mils or less, and preferably about 0.5 to about 5 mils. The elastic member has a recovery at 50% elongation after 3 seconds and preferably instantaneously of at least about 90%, and preferably close to 100%. For ease of stretchability, the modulus of elasticity of the elastic member at 50% elongation should not exceed about 2000 pounds per square inch. The modulus of elasticity is preferably substantially less than 2000 pounds per square inch, and most preferably is about 20 to about 200 pounds per square inch.

It is important that the elastic members in the longitudinal side margins of the diaper be secured so as to not only shorten, e.g., gather, the side margins but also act on the adjacent sides of the absorbent batt to create pillow-like bulges or convolutions that shape the absorbent batt in the perineal region of the infant for comfort and gasketing. The elastic members generally are secured to follow the contour of the side edges of the absorbent batt and to act directly on the sides of the batt when in physical contact therewith, or to act through the backing and/or the facing to constringe the sides of the batt. In any event, the recovery force of an extended elastic member must be sufficient to overcome the resistance to deformation offered by the relatively stiff absorbent batt. And, the relationship between the elastic members and the batt is such that while the elastic members are effective to bulge the sides of the batt, the central region of the batt is not compacted or gathered which would result in the presence of too much bulky material between the legs of the infant and detract from the fit of the diaper. Preferably, the elastic members are secured to extend generally parallel to the adjacent batt side edge so that substantially equal compressive forces are applied to the batt side edges throughout the length of the elastic members.

Any gathering of the diaper side margins that takes place because of the relaxation of elastic bands present in the diaper side margins necessarily increases the thickness dimension of the margins, thereby making effective gasketing difficult, and usually requires an excessive compressive force on the baby's thighs. The diaper construction of the present invention, on the other hand, by providing secured elastic members in the diaper side margins to effectively gather not only the side margins but also the adjacent batt side margins substantially eliminates the possiblity of an undesirable increase in side margin thickness.

In the preferred embodiment of the present invention the constringent means have a width of at least about ¼", preferably a width of at least ½", and more preferably a width of from about ¾" to about 1¼". The width-to-thickness ratio should be at least about 30, preferably about 100, and most preferably about 500 to about 1000.

Referring to FIG. 1, disposable diaper 10 embodying the present invention is provided with marginal longitudinal constringent means in opposite side margins 11 and 12 adapted to provide enhanced fit and gasketing about the baby's thighs. Additionally, optional transverse constringent means are provided in end margins 13 and 14 for enhanced fit about the baby's waist. The constringent means in each of the side margins is a relatively wide but thin elastic member, such as elastic member 15 in side margin 11. The optional transverse constringent means in the end margins of diaper 10 can be a similar elastic member such as member 16 in end margin 14. Diaper 10 additionally includes first outer layer or backing 17 made of a moisture impervious web, a contoured absorbent batt 18 positioned in superposed relationship with respect to the backing, and second outer layer or facing 19 made of a moisture pervious web and positioned in superposed relationship with respect to absorbent batt 18. For securement about a baby, diaper 10 is provied with pressure-sensitive adhesive tape tabs 20. The longitudinal constringent means are generally parallel to the longitudinal side margins of batt 18, and when the constringent means are in a relaxed state, diaper 10 assumes a boat-like configuration, with side margins 11 and 12 having a reduced length, as compared to the flat, as manufactured, configuration shown in FIG. 1. As will be discussed in greater detail hereinbelow, the constringent means also act on the respective adjacent side margins of absorbent batt 18 and longitudinally constringe the side margins of batt 18 creating pillow-like marginal bulges or convolutions therein.

Absorbent batt 18 is superposed over backing 17 and is secured thereto by a series of parallel glue lines 23 deposited on backing 17. Absorbent batt 18 is of smaller area than backing 17 and, when substantially centered on backing 17, is spaced from the longitudinal sides as well as transverse sides or ends of the backing to thereby define the side and end margins of diaper 10. Absorbent batt 18 is flanked on all four sides thereof by elastic film members 15, 16, 21 and 22 which, in an extended state, are secured to backing 17 by one or more rows of spaced securement means, such as an elastic adhesive, sonic sealing, or by any other convenient manner. Moisture pervious facing 19 is superposed over absorbent batt 18, is larger in area than batt 18, and is secured to backing 17, usually by means of the exposed end portions of glue lines 23. However, other securement means can be utilized, if desired. Facing 19 is also secured to elastic film members 15, 16, 21 and 22 in a manner similar to the securement thereof to backing 17.

In a preferred embodiment of the invention the facing and backing have substantially the same shape and size and are coterminous with one another. The absorbent batt is similar in shape to the facing and backing layers and is centered with respect thereto. Since all of the major layers of the diaper have essentially the same geometric configuration, only one layer—the batt 18—will be described in detail.

The end portions 25 and 26 of batt 18 are generally equal in width and are wider than the batt mid-portion 27. For improved fit, the narrowest part 28 of the batt mid-portion is offset toward batt end portion 26, the portion that is adapted to be placed in front of the infant. Batt portion 28 is of relatively short length and is formed between parallel side edges 28a and 28b. Batt side edges 29, 30, 31 and 32 flare outwardly from the ends of edges 28a and 28b and terminate in end portion 29a parallel with end portion 31a and end portion 30a parallel with end portion 32a. In a most preferred embodiment of the invention, edges 29 and 21 are disposed at an angle of 25° and edges 30 and 32 are disposed at an angle of 35°, so that the included angle between edges 29 and 30 and edges 31 and 32 is 120°.

The elastic members 15 and 21 which form the constringent means at opposite sides of the diaper are parallel with the side edges of the batt between the overlapping side edges of layers 17 and 19 for improved application of constringing forces to not only the side margins of the facing and backing layers, but also directly to the sides of the panel 18. The elastic members extend beyond the ends of the panel 18, and completely from end to end of the diaper.

Batt 18 preferably is provided with a densified skin in accordance with the teachings of commonly assigned U.S. Pat. No. 3,938,522 to Repke, the disclosure of which is hereby incorporated herein in its entirety by this reference. Glue lines 23 penetrate the densified skin and cooperate with it to stiffen the mid-portion of the batt and prevent the central portion of the diaper from buckling or gathering under the influence of the constringent means hereinafter described.

As is explained in detail in commonly assigned Mesek et al. application Ser. No. 106,182 filed Dec. 21, 1979, and entitled "Conformable Disposable Diapers Having Absorbent Panel With Bulged Side Members" now U.S. Pat. No. 4,324,245, the disclosure of which is incorporated herein by this reference, the direct action of elastic member 15 on facing 19 and backing 17 secured thereto gathers the resulting laminar composite forming a plurality of gathers or macropleats in side margin 11. At the same time elastic member 15 acts on the adjacent side margin of absorbent batt 18 to produce controlled pillow-like convolutions or bulges at the sides thereof. Because of the aforementioned cooperative action of the densified skin and glue lines, the central portion of the batt and the central portion of the other diaper components are not influenced by the constringent means, and hence remain ungathered. Thus, in accordance with the present invention there is a transition from gathers at opposite side margins of the diaper, to bulges inwardly of the side margins and generally in alignment with opposite sides of the batt, and finally to a relatively smooth and undisturbed diaper mid-portion.

The generally smooth mid-portion of the batt occupies at least 20% of the batt width dimension and preferably from about 50% to about 80%. The bulges in the side margins of the batt have a maximum height dimension at the sides of the batt, and taper generally uniformly inwardly to the generally smooth batt mid-portion. When the diaper is applied to a baby, the partially extended diaper side margins 11 and 12 provide a comfortable yet positive seal about the baby's thighs that readily accommodates leg movements of the baby, while optional elastic members in diaper end margins 13 and 14 assure good fit about the baby's waist.

While elastic members 15 and 21 have been illustrated as being spaced slightly outward from the adjacent batt side edge, it is within the purview of the present invention to locate the elastic members so that a portion thereof underlies the adjacent edges of the absorbent batt to provide direct constringent action on the side margins of the batt when the elastic members are relaxed. If necessary, the side margins of the absorbent batt can be secured, by means of an adhesive or in any other convenient manner, to such underlying portions of the elastic members; however, usually it is not necessary to do so inasmuch as the coefficient of friction between the resulting contiguous surfaces is sufficient to transmit a constringing force from the elastic ribbons to the batt. Usually the absorbent batt would overlie less than about one-half of the width of elastic members.

Referring now to FIG. 3, a further diaper embodiment is illustrated generally at 40 and includes a facing layer 41, a generally identically shaped backing layer 42, and an absorbent panel 43 sandwiched therebetween. The facing layer 41 is, of course, a moisture pervious member, while the backing layer 42, is moisture impervious. Curvilinear cutouts 44 are provided in the central region of the sides of the facing and backing layers, and the portions of the facing and backing layers extending laterally beyond the sides of the panel define the diaper side margins. The absorbent panel 43 has parallel opposite end margins 44 and 45 and parallel opposite longitudinal side margins 46 and 47. Along the longitudinal margins there are disposed indentations 48 and 49. The deepest part of the indentations is approximately one-third along the length of the pad to form a smaller front portion 50 and a larger rear portion 51. The front edge 52 of each indentation is arcuate and the front half of the indentation has the shape of an arc of a circle. In use, the front edge is disposed in the region of the inner and front portion of the baby's leg or thigh to provide a good fit in that area. The rear edge 53 of the indentation is generally uniformly sloped from the deepest part of the indentation to the longitudinal edge portion. In use, this rear edge fits about the rear of the baby's leg or thigh to provide a good fit in that area. The sloped rear edge makes an angle of about 30 to 45 degrees to the center line of the diaper. The sides of the panel adjacent the indentations in the central portion are parallel with one another. This configuration provides the improved fit with a minimum loss of absorptive capacity. Corners 54 contain extended longitudinal side portions which fit about the waist area of the wearer and provide increased absorbent material and capacity in the panel. The size and shape of the corners may vary greatly depending on the type and size of the diaper being produced.

The indentations, depending on whether the diaper is a newborn size, toddler size, or other size, will vary from about an inch to two inches in depth and preferably from about 1¼ to 1¾ inches in depth. The front edge or arc is on a radius similar to the depth or equal to the depth dimension. The distance the deepest part of the indentation may be from the front end margin of the absorbent panel may vary from about four to six inches and from about 30% to 40% of the total length of the panel and preferably from about 30% to 35% of the total length of the panel to provide the desired fit and aesthetically shaped panel. In some embodiments of the indentation, the portion of the front edge which meets the longitudinal side of the panel may be a straight portion; i.e., perpendicular to the side, depending on the size of the diaper being produced. The gently sloped rear edge, where it starts from the deepest part of the indentation, may also be gently rounded before it straightens out to its desired slope, again depending on the size of the diaper being produced. The indentation as described provides a close, neat fit around the wide variety of leg sizes.

The narrowed crotch area; i.e., the dimension of the panel between indentations, may also be varied according to diaper size. This dimension may be as small as 3 to 3½ inches for a newborn size diaper or as large as 4½ inches or more for toddler or other large size diapers. A narrowed crotch area dimension of 3½ to 4 inches is satisfactory for most sizes. In each case the diaper is symmetrical about the longitudinal center line.

Constringent means is provided in each side margin of diaper 40 for not only gathering the side margins of the diaper, but also for creating pillow-like bulges in the sides of the panel, as described above. As with the previously described embodiment, the constringent means are in the form of longitudinally extending, wide, flat elastic members 55 disposed in the side margins of the diaper and extending parallel to the adjacent side edge of the panel for direct application of constringing forces to the panel side margins. The ends of the elastic members may ovelap the corners of the panel, as shown in 55a in FIG. 3.

Figure 2:
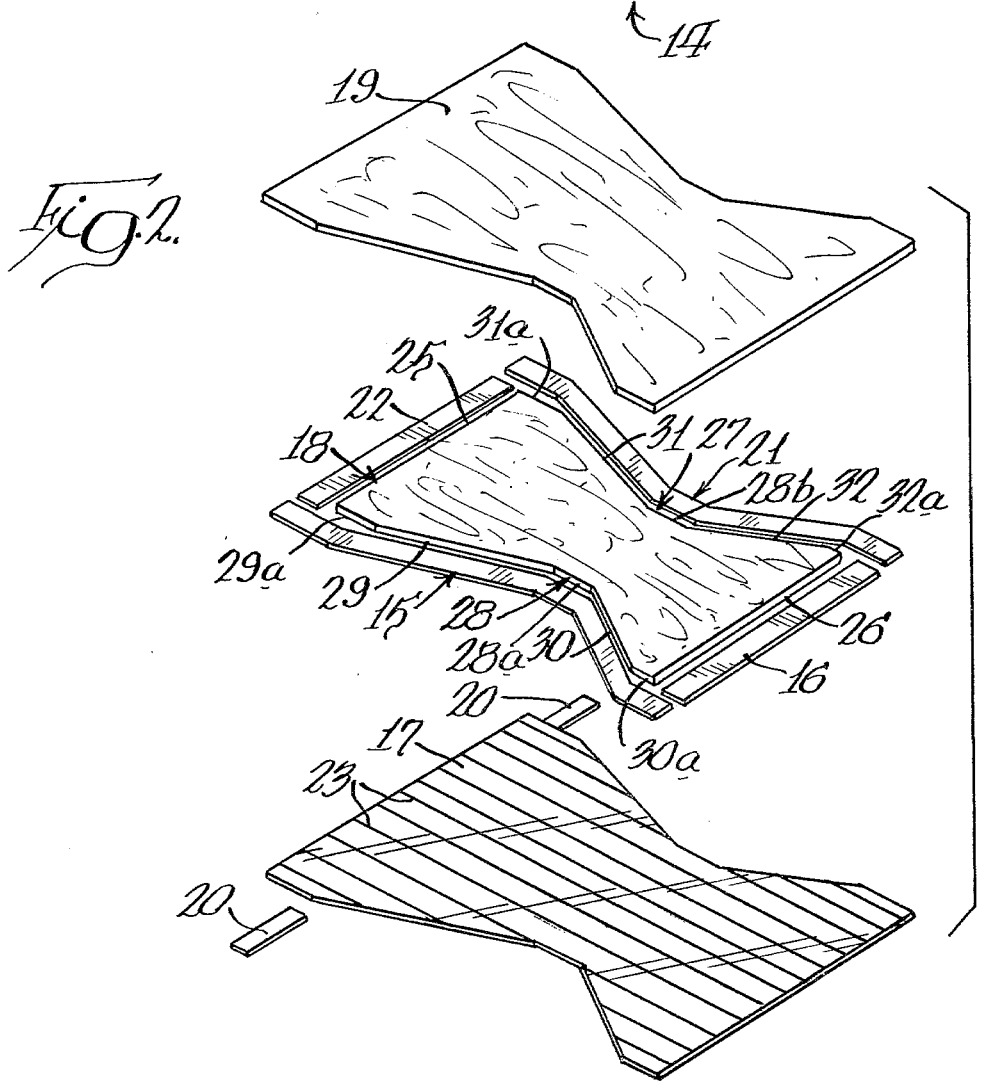
FIG. 2 is an exploded perspective view showing relative positioning of diaper elements during manufacture of the diaper illustrated in FIG. 1.

While absorbent panels of the type illustrated in FIGS. 1-3 are preferred because of improved fit characteristics that are imparted to the diaper, the present invention is not limited thereto, and absorbent panels of the type shown in FIGS. 4-6 are also contemplated. Such latter panels are designated in their entirety by reference numeral 60, and have a reduced width intermediate portion defined between indentations 61 at opposite sides of the diaper. The facing and backing layers of such diapers may have a shape similar to the shape of the absorbent panel, or a modified shape but what is important for purposes of the present invention is that there be a constringent means secured in each side margin of the diaper, such as elastic member 64 in FIG. 4, and that the constrigent means include an inwardly offset portion, such as 65 in FIG. 4, in the region of the panel indentations 61 for application of constringing forces to the sides of the panel between the baby's thighs. It should also be noted that while the elastic member 64 is spaced equally outwardly from the adjacent panel edge throughout the length of the elastic member, the end portions 64a (FIG. 5) may be positioned more closely to the side edge of the panel than the mid-portion 64b, or the midportion 64c (FIG. 6) may be positioned more closely to the side edge of the panel than end portions 64d. Constringent means is provided in each side margin of diaper 40.

Elastic film members suitable as constringing elements for the diapers contemplated herein can be extruded to the desired thickness utilizing unvulcanized, thermoplastic compositions which are made up of an elastomeric component and an optional compatible modifier which is a thermoplastic polymer of a relatively low molecular weight but solid at ambient temperature.

Illustrative of the elastomeric components suitable for present purposes are block copolymers which comprise terminal thermoplastic polymer blocks and at least one non-terminal or intermediate elastomeric polymer block. Block copolymers of this general type may be prepared using a step-wise polymerization initiator, e.g., an organolithium compound. Such block polymerization techniques are well known in the art.

The elastomeric component can be linear or radial $A^1$-B-$A^2$ block copolymers or mixtures thereof with simple $A^1$-B block copolymers where $A^1$ and $A^2$ can be alike or different and represent a thermoplastic polymer block, such as poly (vinylarene) block, and B represents an elastomeric polymer block such as a conjugated diene or a lower (i.e., $C_1$–$C_4$) alkene. The modifier component is a low molecular weight thermoplastic polymer having an average molecular weight of about 500 to about 7,500 and is present in the composition in an amount of about zero to about 200 parts by weight per 100 parts by weight of the elastomeric component.

A preferred thermoplastic film composition for the elastic film members comprises an elastomeric component which contains, as a major constitutent thereof, an unvulcanized linear block copolymer of the general configuration

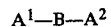

$$A^1-B-A^2$$

wherein $A^1$, $A^2$ and B have the same meaning as hereinabove. In these block copolymers the A-blocks are derived from styrene or styrene homologues, and the B-blocks are derived from conjugated dienes or lower alkenes. The thermoplastic polymer modifier is compatible with the elastomeric component and associates principally with the thermoplastic terminal blocks of the aforesaid unvulcanized block copolymer. The thermoplastic polymer modifier preferably has an average molecular weight of about 1000 to about 3000, and is present in the film composition in an amount of about 80 to about 200 parts by weight per 100 parts by weight of the elastomeric component.

The preferred $A^1$-B-$A^2$ block copolymers have A-blocks derived, i.e., polymerized or copolymerized, from styrene or styrene homologues; and B-blocks derived from conjugated dienes, such as isoprene or butadiene, or from lower alkenes, such as ethylene and butylene. Small proportions of other monomers also may enter into the block copolymers themselves. The individual A-blocks can have an average molecular weight of at least about 6000, preferably in the range of about 8000-30,000, and the A-blocks constitute about 5-50%. preferably about 10-30%, by weight of the block copolymer. The average molecular weight of the B-blocks of linear $A^1$-B-$A^2$ block copolymers preferably is in the range of about 45,000-180,000 and that of the linear copolymer itself preferably is in the range of about 75,000-200,000. The average molecular weight of the radial $A^1$-B-$A^2$ block copolymers preferably is in the range of about 125,000-400,000. The term "linear block copolymer" (or copolymers) includes branched $A^1$-B-$A^2$ copolymers as well as unbranched $A^1$-B-$A^2$ copolymers.

The radial $A^1$-B-$A^2$ copolymers useful for manufacture of elastic members for diapers of this invention are of the type described in U.S. Pat. No. 3,281,383 to Zelinski et al. and conform to the following general formula: $(A-B-)_nX$, wherein A is a thermoplastic block polymerized from styrene or styrene homologues, B is an elastomeric block derived from conjugated dienes or lower alkenes, as indicated above, X is an organic or inorganic connecting molecule, with a functionality of about 2 to 4 as described in U.S. Pat. No. 3,281,383, or possibly with a higher functionality as described in the article entitled "New Rubber is Backed by Stars" appearing on page 35 of the June 11, 1975 issued of *Chemical Week*. As used hereinabove, "n" has a value corresponding to the functionality of X.

The preferred elastic film member is highly thermoplastic and, though elastomeric, is unlike rubber in that the film exhibits a relatively sharp melting point and is capable of being heat shaped. Also, the elastic film member can form permanent heat seals to substrates such as non-woven fabrics, or the like, at relatively low heat sealing peak temperatures, generally not above about 350° F. The film member is highly elastic and has a relatively low rubber modulus, i.e., to exhibits in at least one direction an elastic recovery from 50% stretch to at least 75%, preferably at least about 80%, and a 50% rubber modulus of not above about 2000 pounds per square inch, preferably not above 1000 pounds per square inch at 50% elongation. The film member also is very flexible, extensible and soft and normally exhibits a Gurley stiffness of about one or less at a film thickness of one mil, and an elongation to break of at least about 300%, preferably at least about 400%, in at least one direction at ambient temperatures.

While the constringent means described above is in the form of a single elastic ribbon at opposite sides of the diaper, the present invention is not limited thereto, and it is contemplated that other forms of constringent means may be provided, so long as the constringent means is effective to bulge the side margins of the batt. In this regard, it is contemplated that each side margin of the diaper may include a plurality of secured, spaced, parallel longitudinally extending elastic members; such as, bands, round or flattened tubes, monofilaments, etc.

By way of example, and with reference to FIG. 1, the illustrated ribbons 15 and 21 may be replaced by a pair of ¼" wide elastic bands that are parallel with one another and with the adjacent side edge of the batt. With such an arrangement, the innermost elastic bands would be disposed directly adjacent to the side edge of the batt, and the center lines of the bands would be spaced from one another by ¾". It will be recognized that such a constringent means is less costly than a construction that uses a 1" wide elastic member, because less material is utilized. Nevertheless, it is possible to efect the desired gathering at the sides of the diaper, and bulging of the side margins of the batt, without undue stress concentration upon an infant's skin, since the pulling force of the plural elastic members is distributed over a relatively large area. Stated differently, the desired results of the invention can be achieved by the use of plural elastic members at each side of the diaper, since the pulling force required for each elastic member is less than that required for a single elastic member and the amount of pre-stretch for the individual plural elastic members can be reduced accordingly. With such an arrangement it is also possible to pre-stretch the elastic members a different amount, if desired or necessary, to achieve the desired panel bulging effect.

Several different types of facing materials may be used for diaper facing. For example, the facing may be a non-woven web made up of a mixture of fibers consisting predominantly of inexpensive short cellulosic fibers such as wood pulp fibers or cotton linters, in amounts of about 75% to about 98%, the balance being textile length fibers such as rayon as described in U.S. Pat. No. 3,633,348 to Liloia et al.

Non-woven facing materials suitable for use in disposable diapers of this invention can have fabric weights in the range of about 0.5 to 5 oz./yd.$^2$ and densities of less than 0.15 g./cc., generally in the range of about 0.05 to about 0.1 g./cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness, and drape characteristics.

Facings may also be made of an apertured, non-woven fabric which is formed, for example, in accordance with the teachings of commonly assigned U.S. Pat. Nos. 2,862,251; 3,081,514 and 3,081,515. Briefly, such fabrics are foraminous structures wherein groups or groupings of fibers have been rearranged from a fibrous non-woven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a fibrous polyester type material can have a weight of about 0.75 oz./yd.$^2$.

In addition, facings can be formed of a non-apertured material, such as a non-woven isotropic web, or of an apertured polyolefin or polyester film having the desired moisture permeability. In all of the aforementioned facings the material should be relatively hydrophobic so as to retard wicking within the facing.

The moisture-absorbent batt or panel of a desired shape but smaller than the facing and the backing, can be formed in accordance with the teachings of U.S. Pat. No. 3,612,055 to Mesek et al.

A suitable backing material for the diapers embodying the present invention can be an opaque polyolefin, e.g., polyethylene, web about 0.001 inch thick. Another suitable material for this purpose is a polyethylene terephthalate web having a thickness of about 0.0005 inch.

In use, the disposable diaper is applied to the baby by laying out the diaper on a suitable flat surface and placing the baby thereon so that the waist-underlying end of the diaper is that having the fastener means. The other end of the diaper then extends downwardly between the infant's legs. Next, the downwardly extending end of the diaper is brought up between the baby's legs to a position covering the perineum and contiguous with the front portion of the baby's waist. The diaper is thereafter secured to the baby by placing the corners of the waist portion of the abdomen-covering end as far around the baby's waist as they will go and by bringing the corners of the underlying end of the diaper into an overlapping relationship with the aforementioned corners so that the diaper snugly encircles the baby's waist and provides a custom fit. The adhesive tab fasteners are then prepared for use and the diaper is secured in the desired position by simply urging the pressure-sensitive adhesive surface of the tape tab in contact with the adjacent outer surface of the opposite corner of the diaper.

The foregoing description and the drawings are illustrative and are not to be taken as limiting. Still other variations and modifications are possible without departing from the spirit and scope of the present invention.

We claim:

1. A disposable diaper comprising: a moisture pervious facing layer adapted to be positioned adjacent the skin of an infant, a moisture impervious backing layer secured to said facing layer, an absorbent batt positioned between said facing and backing layers, said batt being smaller than said facing and backing layers and spaced inwardly from the ends and sides thereof, said batt having a length dimension greater than its width dimension, the end portions of said batt being wider than an intermediate portion thereof and said intermediate portion being offset longitudinally toward one end of the batt, said batt having longitudinal side edges including parallel side edge segments defining said intermediate portion and further outwardly extending side edge segments from opposite ends of said parallel side edge segments terminating in still further parallel side edge segments extending from the ends of said outwardly extending side edge segments and terminating at the ends of said batt, said still further parallel side edge segments at opposite sides of said batt being spaced equally from the longitudinal center line of the batt, said outwardly extending side edge segments forming straight lines at opposite sides of said batt being spaced equally from the longitudnal center line of the batt and disposed at an equal angle, whereby said batt is symmetrical about its longitudinal center line, and continuous longitudinally extending elastic means secured at each side of the diaper immediately adjacent the batt and parallel to a respective said longitudinal side edge, whereby the sides of said diaper are gathered and said diaper has improved fit between the thighs when applied to an infant.

2. A disposable diaper as claimed in claim 1 wherein the end portions of said facing and backing layers are wider than an intermediate portion thereof.

3. A disposable diaper as claimed in claim 2 wherein the longitudinal side edges of said facing and backing layers are generally parallel with the longitudinal side edges of the batt.

4. A disposable diaper as claimed in claim 3 wherein said facing and backing layers are generally coextensive with one another.

* * * * *